US012656299B2

(12) United States Patent
Onishi et al.

(10) Patent No.: US 12,656,299 B2
(45) Date of Patent: Jun. 16, 2026

(54) GAS SENSOR ELEMENT AND GAS SENSOR

(71) Applicant: NGK INSULATORS, LTD., Nagoya (JP)

(72) Inventors: Ryo Onishi, Iwakura (JP); Kaoru Shibutani, Nagoya (JP)

(73) Assignee: NGK INSULATORS, LTD., Nagoya (JP)

( * ) Notice: Subject to any disclaimer, the term of this patent is extended or adjusted under 35 U.S.C. 154(b) by 220 days.

(21) Appl. No.: 18/467,042

(22) Filed: Sep. 14, 2023

(65) Prior Publication Data

US 2024/0003841 A1 Jan. 4, 2024

Related U.S. Application Data

(63) Continuation of application No. PCT/JP2022/006368, filed on Feb. 17, 2022.

(30) Foreign Application Priority Data

Mar. 16, 2021 (JP) ................................. 2021-042258

(51) Int. Cl.
*G01N 27/407* (2006.01)
*G01N 27/30* (2006.01)
*G01N 27/41* (2006.01)
*G01N 33/00* (2006.01)

(52) U.S. Cl.
CPC ....... *G01N 27/4077* (2013.01); *G01N 27/304* (2013.01); *G01N 27/41* (2013.01); *G01N 33/0027* (2013.01)

(58) Field of Classification Search
CPC .. G01N 27/4077; G01N 27/304; G01N 27/41; G01N 33/0027; G01N 33/0037; F01N 2510/00; F01N 2560/026; F01N 11/00
See application file for complete search history.

(56) References Cited

U.S. PATENT DOCUMENTS

| 2015/0268187 A1 | 9/2015 | Adachi et al. | |
| 2017/0284958 A1* | 10/2017 | Watanabe | .......... G01N 27/4074 |
| 2018/0284055 A1* | 10/2018 | Hino | .................. G01N 27/4072 |
| 2020/0271618 A1 | 8/2020 | Onishi et al. | |

FOREIGN PATENT DOCUMENTS

| CN | 111610243 A | 9/2020 | |
| JP | 2011-214853 A | 10/2011 | |
| JP | 2012173146 A * | 9/2012 | .......... G01N 27/4071 |

(Continued)

OTHER PUBLICATIONS

Mitsuoka et al., JP2012173146A, English translation, 2012 (Year: 2012).*

(Continued)

*Primary Examiner* — Shizhi Qian
(74) *Attorney, Agent, or Firm* — MATTINGLY & MALUR, PC

(57) ABSTRACT

A sensor element includes: an element body including an oxygen-ion-conductive solid electrolyte layer; and a protective layer that covers at least part of the element body and is a porous body having a plurality of pores thereinside. The standard deviation of the porosity of the protective layer is 2.3% or less.

12 Claims, 5 Drawing Sheets

(56)  References Cited

FOREIGN PATENT DOCUMENTS

| | | | |
|---|---|---|---|
| JP | 2013-36940 | A | 2/2013 |
| JP | 2013-54025 | A | 3/2013 |
| JP | 2015-178988 | A | 10/2015 |
| JP | 2016-065852 | A | 4/2016 |
| JP | 2017-187482 | A | 10/2017 |
| JP | 2018-112492 | A | 7/2018 |

OTHER PUBLICATIONS

International Search Report of PCT/JP2022/006368 dated Apr. 5, 2022.
International Preliminary Report on Patentability and Written Opinion received in corresponding International Application No. PCT/JP2022/006368 dated Sep. 28, 2023.
Chinese Office Action received in corresponding Chinese Application No. 202280008013.6 dated Dec. 24, 2025.

* cited by examiner

GAS SENSOR ELEMENT AND GAS SENSOR

CROSS-REFERENCE TO RELATED APPLICATION

This application is a continuation application of PCT/JP2022/006368, filed on Feb. 17, 2022, which claims the benefit of priority of Japanese Patent Application No. 2021-042258, filed on Mar. 16, 2021, the entire contents of which are incorporated herein by reference.

BACKGROUND OF THE INVENTION

1. Field of the Invention

The present invention relates to a gas sensor element and a gas sensor.

2. Description of the Related Art

A gas sensor including a gas sensor element that detects the concentration of a specific gas such as NOx in a measurement-object gas such as exhaust gas from automobiles is a known art. In one known gas sensor, a porous protective layer is formed on the surface of the gas sensor element (for example, PTL 1). PTL 2 describes a porous protective layer having a two-layer structure including an inner protective layer and an outer protective layer. The porous protective layer plays a role in preventing the occurrence of cracking in the sensor element due to adhesion of water.

CITATION LIST

Patent Literature

PTL 1: Japanese Unexamined Patent Application Publication No. 2016-065852
PTL 2: Japanese Unexamined Patent Application Publication No. 2017-187482

SUMMARY OF THE INVENTION

In recent years, there is a demand to detect the concentration of a specific gas even when a large amount of water is present around the gas sensor element, and there is a need for a gas sensor element having higher waterproofing performance.

The present invention has been made to solve the foregoing problem, and it is a main object of the invention to improve the waterproofing performance of a gas sensor element.

To achieve the above main object, the present invention employs the following measures.

The gas sensor element of the present invention includes: an element body including an oxygen-ion-conductive solid electrolyte layer; and a protective layer that covers at least part of the element body and is a porous body having a plurality of pores thereinside, wherein the standard deviation of the porosity of the protective layer is 2.3% or less.

This gas sensor element includes the protective layer in which the standard deviation of the porosity is 2.3% or less, i.e., variations in the porosity are small. Since the standard deviation of the porosity is 2.3% or less, the volume of partial portions whose porosity is small, i.e., partial portions whose heat insulating ability is low, is small, so that the degree of cooling of the element body when moisture adheres to the gas sensor element is reduced. Therefore, the waterproofing performance of the gas sensor element is improved.

In the gas sensor element of the invention, the element body may have an elongate rectangular parallelepiped shape and may include a measurement-object gas flow portion that is formed inside the element body and through which a measurement-object gas introduced thereinto flows. The protective layer may cover a closest surface of the element body that is one of four surfaces thereof extending in a longitudinal direction of the element body and that is closest to the measurement-object gas flow portion. In the protective layer, the standard deviation of the porosity in a portion that covers a region of the closest surface onto which the measurement-object gas flow portion is projected may be 2.3% or less. In the element body, the strength of a portion between the closest surface and the measurement-object gas flow portion is low, and this portion is relatively vulnerable to thermal shock. In the protective layer, the standard deviation of the porosity in the portion that covers the region of the closest surface onto which the measurement-object gas flow portion is projected is 2.3% or less. Therefore, the occurrence of cracking in the portion vulnerable to thermal shock can be reduced, so that the waterproofing performance of the gas sensor element is improved. In the gas sensor element in this aspect, it is only necessary that the standard deviation of the porosity be 2.3% or less in at least the above portion of the protective layer. For example, portions in which the standard deviation exceeds 2.3% may be present in other portions of the protective layer that cover other regions (e.g., regions of the closest surface other than the above region).

In the gas sensor element of the invention, the element body may have an elongate rectangular parallelepiped shape and may include a measurement-object gas flow portion that is formed inside the element body and through which a measurement-object gas introduced thereinto flows. A gas inlet that is an inlet of the measurement-object gas flow portion may have an opening on a longitudinal end surface of the element body, and the protective layer may cover the end surface of the element body. In the protective layer, the standard deviation of the porosity in a portion that covers the end surface may be 2.3% or less. In the element body, the strength of a portion around the gas inlet is low, and this portion is relatively vulnerable to thermal shock. In the protective layer, the standard deviation of the porosity in the portion that covers the longitudinal end surface of the element body on which the gas inlet has its opening is 2.3% or less. Therefore, the occurrence of cracking in the portion vulnerable to thermal shock can be reduced, so that the waterproofing performance of the gas sensor element is improved.

In the gas sensor element of the invention, the porosity of the protective layer may be from 10% to 40% inclusive. In the gas sensor element of the invention, the protective layer may have a thickness of from 100 μm to 500 μm inclusive.

In the gas sensor element of the invention, the protective layer may include a porous inner protective layer and a porous outer protective layer that is located outward of the inner protective layer and has a smaller porosity than the inner protective layer. In the protective layer, the standard deviation of the porosity in the inner protective layer may be 2.3% or less. In this case, since the porosity of the outer protective layer is small, moisture does not easily pass through the outer protective layer. Since the porosity of the inner protective layer is large, its heat insulating ability is high, so that the waterproofing performance of the gas sensor element is improved. Moreover, since the standard deviation of the porosity in the inner protective layer is 2.3% or less, the volume of partial portions whose porosity is small, i.e., partial portions whose heat insulating ability is low, in the inner protective layer is small, the waterproofing performance of the gas sensor element is further improved. In the gas sensor element in this aspect, it is unnecessary that the standard deviation of the porosity of the outer protective layer be 2.3% or less.

In the gas sensor element of the invention, the element body may have an elongate rectangular parallelepiped shape and may include a measurement-object gas flow portion that is formed inside the element body and through which a measurement-object gas introduced thereinto flows. The inner protective layer may cover a closest surface of the element body that is one of four surfaces thereof extending in a longitudinal direction of the element body and that is closest to the measurement-object gas flow portion. In the inner protective layer, the standard deviation of the porosity in a portion that covers a region of the closest surface onto which the measurement-object gas flow portion is projected may be 2.3% or less. In the element body, the strength of the portion between the closest surface and the measurement-object gas flow portion is low, and this portion is relatively vulnerable to thermal shock. In the inner protective layer, the standard deviation of the porosity in the portion that covers the region of the closest surface onto which the measurement-object gas flow portion is projected is 2.3% or less. Therefore, the occurrence of cracking in the portion vulnerable to thermal shock can be reduced, so that the waterproofing performance of the gas sensor element is improved. In the gas sensor element in this aspect, it is only necessary that the standard deviation of the porosity be 2.3% or less in at least the above portion of the inner protective layer. For example, portions in which the standard deviation exceeds 2.3% may be present in other portion of the inner protective layer that cover other regions (e.g., regions of the closest surface other than the above region).

In the gas sensor element of the invention, the element body may have an elongate rectangular parallelepiped shape and may include a measurement-object gas flow portion that is formed inside the element body and through which a measurement-object gas introduced thereinto flows. A gas inlet that is an inlet of the measurement-object gas flow portion may have an opening on a longitudinal end surface of the element body, and the inner protective layer may cover the end surface of the element body. In the inner protective layer, the standard deviation of the porosity in a portion that covers the end surface may be 2.3% or less. In the element body, the strength of the portion around the gas inlet is low, and this portion is relatively vulnerable to thermal shock. In the inner protective layer, the standard deviation of the porosity in the portion that covers the longitudinal end surface of the element body on which the gas inlet has its opening is 2.3% or less. Therefore, the occurrence of cracking in the portion vulnerable to thermal shock can be reduced, so that the waterproofing performance of the gas sensor element is improved.

In the gas sensor element of the invention in the aspect in which the protective layer includes the outer protective layer and the inner protective layer, the porosity of the inner protective layer may be from 40% to 70% inclusive. When the porosity of the inner protective layer is 40% or more, heat insulating effect between the outer protective layer and the element body can be prevented from becoming insufficient. When the porosity of the inner protective layer is 70% or less, the strength of the inner protective layer can be prevented from becoming insufficient.

In the gas sensor element of the invention in the aspect in which the protective layer includes the outer protective layer and the inner protective layer, the inner protective layer may have a thickness of from 300 μm to 700 μm inclusive. The outer protective layer may have a thickness of from 100 μm to 300 μm inclusive.

In the gas sensor element of the invention, the standard deviation may be 1.5% or less. In this case, the waterproofing performance of the gas sensor element is further improved.

The gas sensor of the present invention includes the gas sensor element in any of the above aspects. Therefore, this gas sensor has the same effects as those of the above-described gas sensor element of the invention and, for example, has the effect of improving the waterproofing performance of the sensor element.

DETAILED DESCRIPTION OF THE INVENTION

Figure 1:
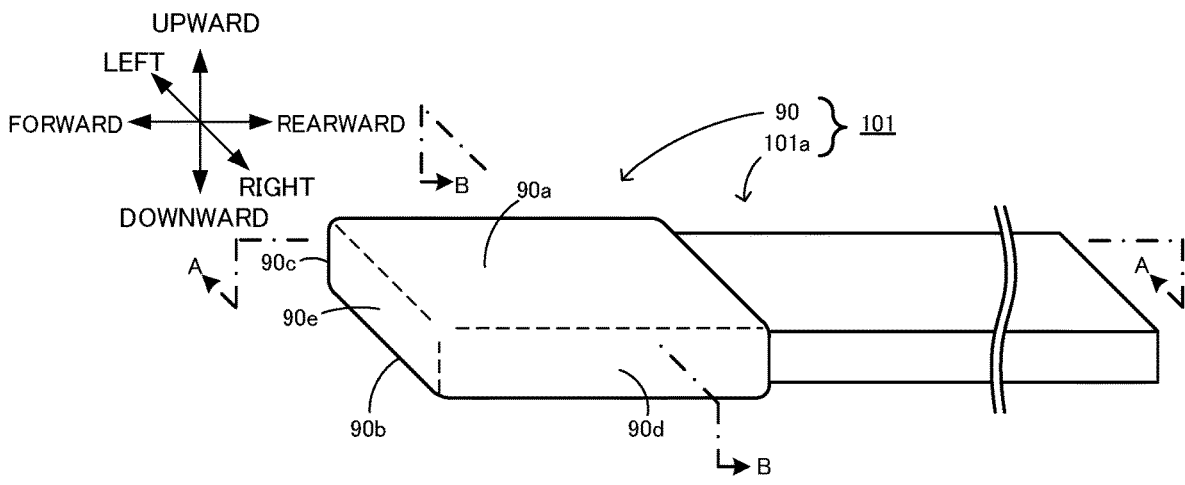
FIG. 1 is a perspective view schematically showing an example of the structure of a sensor element 101.
Figure 2:
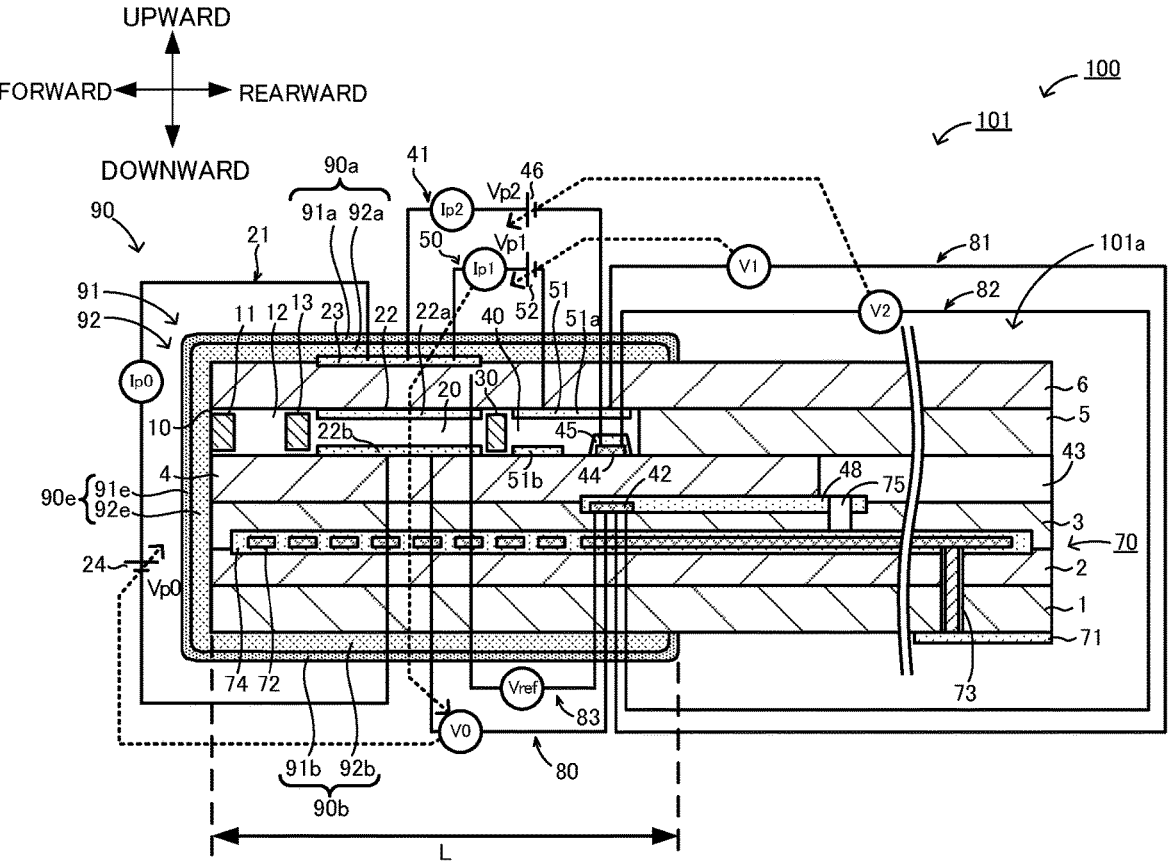
FIG. 2 is a cross-sectional view schematically showing an example of the structure of a gas sensor 100.
Figure 3:
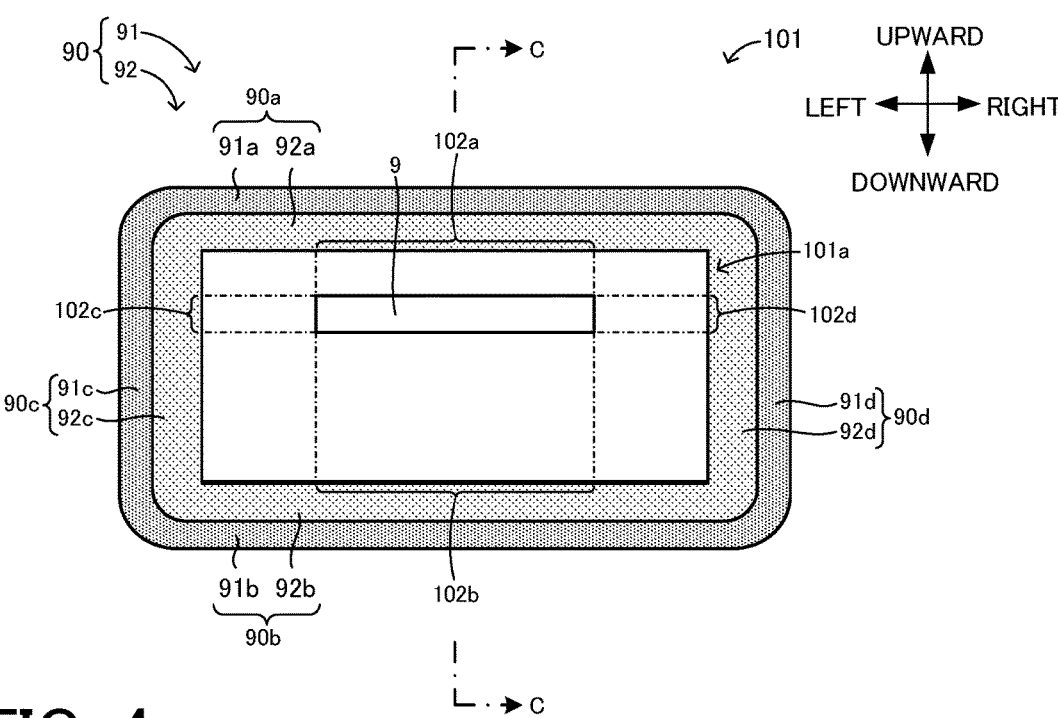
FIG. 3 is a cross-sectional view taken along B-B in FIG. 1.
Figure 4:
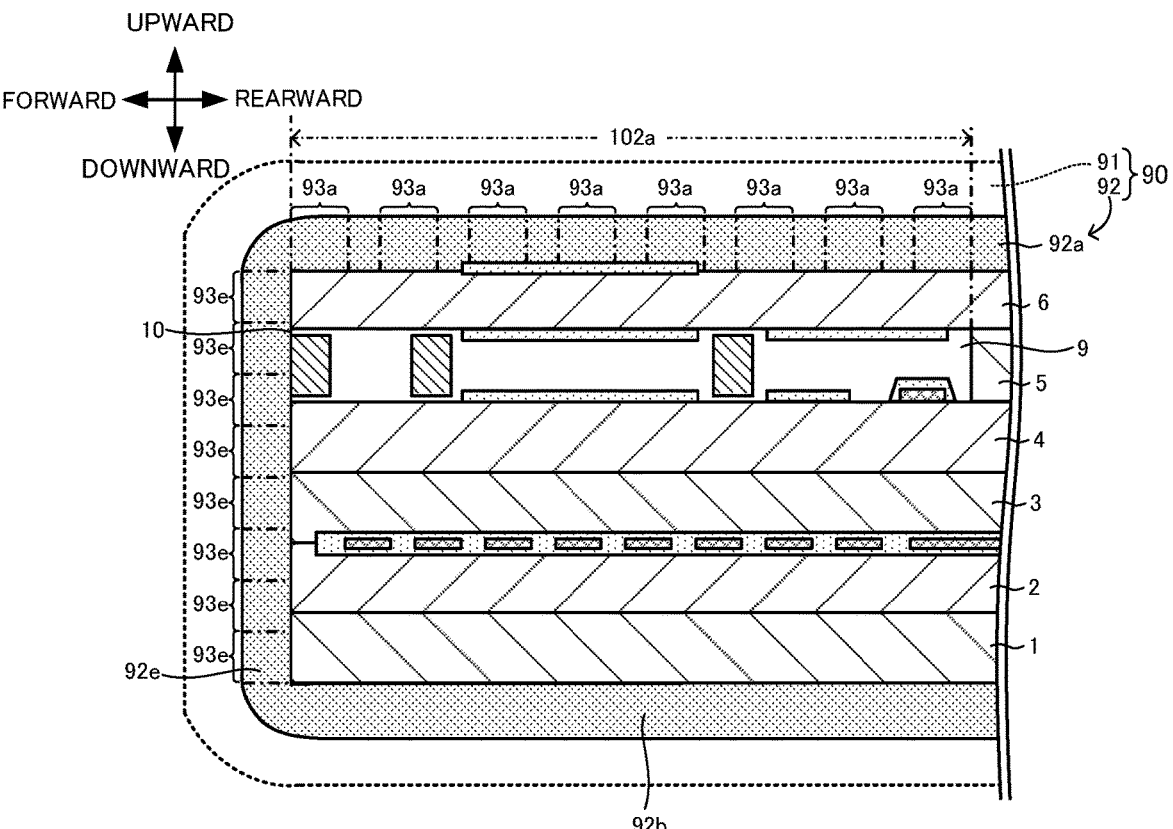
FIG. 4 is a cross-sectional view taken along C-C in FIG. 3.

Next, embodiments of the present invention will be described using the drawings. FIG. 1 is a perspective view schematically showing an example of the structure of a sensor element 101 that is one embodiment of the present invention. FIG. 2 is a cross-sectional view schematically showing an example of the structure of a gas sensor 100 including the sensor element 101 (an example of the gas sensor element of the invention). In FIG. 2, the cross section of the sensor element 101 corresponds to a cross section taken along A-A in FIG. 1. FIG. 3 is a cross-sectional view taken along B-B in FIG. 1. FIG. 4 is a cross-sectional view taken along C-C in FIG. 3. FIG. 4 is also a partial enlarged view of FIG. 2. In FIG. 4, only the outline of an outer protective layer 91 is shown by a broken line. The sensor element 101 has an elongate rectangular parallelepiped shape. The longitudinal direction of the sensor element 101 (the left-right direction in FIG. 2) is defined as a forward-rearward direction, and the thickness direction of the sensor element 101 (the upward-downward direction in FIG. 2) is defined as an upward-downward direction. Moreover, the width direction of the sensor element 101 (a direction perpendicular to the forward-rearward direction and the upward-downward direction) is defined as a left-right direction.

The gas sensor 100 is, for example, attached to a pipe, such as an exhaust pipe of a vehicle, and is used to measure the concentrations of specific gases, such as NOx and $O_2$, contained as the gases to be measured in the exhaust gas. In this embodiment, the gas sensor 100 is designed to measure the NOx concentration as the specific gas concentration. The sensor element 101 includes an element body 101a and a porous protective layer 90 that covers the element body 101a.

As illustrated in FIG. 2, the sensor element 101 is an element having a stack (element body 101a) in which six layers composed of a first substrate layer 1, a second substrate layer 2, a third substrate layer 3, a first solid electrolyte layer 4, a spacer layer 5, and a second solid electrolyte layer 6, each being formed from an oxygen ion-conductive solid electrolyte layer of zirconia ($ZrO_2$) or the like, are stacked in that order from the bottom side in FIG. 2. Also, the solid electrolyte constituting these six layers is dense and airtight. The above-described element body 101a is produced by, for example, subjecting ceramic green sheets corresponding to the individual layers to predetermined processing, printing of circuit patterns, and the like, stacking them thereafter, and further performing firing so as to integrate the ceramic green sheets.

In one front end portion (frontward end portion) of the element body 101a and between the lower surface of the second solid electrolyte layer 6 and the upper surface of the first solid electrolyte layer 4, a gas inlet 10, a first diffusion control section 11, a buffer space 12, a second diffusion control section 13, a first internal cavity 20, a third diffusion control section 30, and a second internal cavity 40 are formed in that order so as to adjoin and communicate.

The gas inlet 10, the buffer space 12, the first internal cavity 20, and the second internal cavity 40 are spaces in the inside of the element body 101a by hollowing the spacer layer 5, where the upper portion is defined by the lower surface of the second solid electrolyte layer 6, the lower portion is defined by the upper surface of the first solid electrolyte layer 4, and the side portions are defined by the side surfaces of the spacer layer 5.

The first diffusion control section 11, the second diffusion control section 13, and the third diffusion control section 30 are each provided as two horizontally extending slits (each of which is a hole whose longitudinal direction is perpendicular to the drawing sheet). The gas inlet 10 is also provided as two horizontally extending holes, as is the first diffusion control section 11. A space extending from the gas inlet 10 to the second internal cavity 40 is referred to as a measurement-object gas flow portion 9. The measurement-object gas flow portion 9 is formed into a substantially rectangular parallelepiped shape. The longitudinal direction of the measurement-object gas flow portion 9 is parallel to the forward-rearward direction.

Meanwhile, at the position farther from the front end side than the measurement-object gas flow portion 9, a reference gas introduction space 43 is provided at the location between the upper surface of the third substrate layer 3 and the lower surface of the spacer layer 5, where the side portions are defined by the side surfaces of the first solid electrolyte layer 4. For example, the air serving as the reference gas at the time of measurement of the NOx concentration is introduced into the reference gas introduction space 43.

An atmosphere introducing layer 48 is a layer composed of porous ceramics. The reference gas is introduced into the atmosphere introducing layer 48 through the reference gas introduction space 43. Also, the atmosphere introducing layer 48 is formed so as to cover a reference electrode 42.

The reference electrode 42 is an electrode formed so as to be sandwiched between the upper surface of the third substrate layer 3 and the first solid electrolyte layer 4 and, as described above, the atmosphere introducing layer 48 connected to the reference gas introduction space 43 is provided around the reference electrode 42. In addition, as described later, it is possible to measure the oxygen concentrations (oxygen partial pressures) in the first internal cavity 20 and the second internal cavity 40 by using the reference electrode 42.

In the measurement-object gas flow portion 9, the gas inlet 10 is a part made open to the outside space, and the gas to be measured is taken from the outside space into the element body 101a through the gas inlet 10. The first diffusion control section 11 is a part for giving predetermined diffusion resistance to the gas to be measured, where the gas is taken from the gas inlet 10. The buffer space 12 is a space provided so as to lead the gas to be measured, where the gas is introduced from the first diffusion control section 11, to the second diffusion control section 13. The second diffusion control section 13 is a part for giving predetermined diffusion resistance to the gas to be measured, where the gas is introduced from the buffer space 12 to the first internal cavity 20. When the gas to be measured is introduced from the outside of the element body 101a into the first internal cavity 20, the gas to be measured, which is taken into the element body 101a through the gas inlet 10 rapidly because of the pressure fluctuation of the gas to be measured in the outside space (pulsation of an exhaust pressure in the case where the gas to be measured is an automotive exhaust gas), is not directly introduced into the first internal cavity 20 but introduced into the first internal cavity 20 after pressure variations of the gas to be measured are canceled through the first diffusion control section 11, the buffer space 12, and the second diffusion control section 13. Consequently, pressure variations of the gas to be measured, which is introduced into the first internal cavity 20, are made to be at an almost negligible level. The first internal cavity 20 is provided as a space for adjusting the oxygen partial pressure in the gas to be measured which is introduced through the second diffusion control section 13. The above-described oxygen partial pressure is adjusted by actuation of a main pump cell 21.

The main pump cell 21 is an electrochemical pump cell including: an inner pump electrode 22 having a ceiling electrode section 22a that is provided over substantially the entire lower surface portion of the second solid electrolyte layer 6 that faces the first internal cavity 20; an outer pump electrode 23 provided on the outer side of the element body 101a in a region of the upper surface of the second solid electrolyte layer 6 that corresponds to the ceiling electrode section 22a; and the second solid electrolyte layer 6 held between these electrodes. The outer pump electrode 23 is disposed on the upper surface of the element body 101a.

The inner pump electrode 22 is formed so as to extend over the upper and lower solid electrolyte layers (second solid electrolyte layer 6 and first solid electrolyte layer 4) defining the first internal cavity 20 and the spacer layer 5 providing the side walls. Specifically, the ceiling electrode section 22a is formed on the lower surface of the second solid electrolyte layer 6 providing the ceiling surface of the first internal cavity 20 and a bottom electrode 22b is formed on the upper surface of the first solid electrolyte layer 4 providing the bottom surface. Then, side electrode portions (not shown in the drawing) are formed on the side wall surfaces (inner surfaces) of the spacer layer 5 constituting both side wall portions of the first internal cavity 20 so as to connect the ceiling electrode section 22a to the bottom electrode 22b. Thus, the inner pump electrode 22 is disposed in the form of a tunnel-like structure in a zone where the side electrode portions are disposed.

The inner pump electrode 22 and the outer pump electrode 23 are formed as porous cermet electrodes (for example, a cermet electrode of Pt containing 1% of Au and $ZrO_2$). In this regard, the inner pump electrode 22 to contact with the gas to be measured is formed by using a material having weakened ability to reduce NOx components in the gas to be measured.

In the main pump cell 21, oxygen in the first internal cavity 20 can be pumped out to the outside space or oxygen in the outside space can be pumped into the first internal cavity 20 by applying a predetermined pump voltage Vp0 between the inner pump electrode 22 and the outer pump electrode 23 and passing a pump current Ip0 between the inner pump electrode 22 and the outer pump electrode 23 in the positive direction or negative direction.

In addition, in order to detect the oxygen concentration (oxygen partial pressure) in the atmosphere in the first internal cavity 20, an electrochemical sensor cell, that is, a main pump controlling oxygen partial pressure detection sensor cell 80 is constructed by the inner pump electrode 22, the second solid electrolyte layer 6, the spacer layer 5, the first solid electrolyte layer 4, the third substrate layer 3, and the reference electrode 42.

The oxygen concentration (oxygen partial pressure) in the first internal cavity 20 is determined by measuring the electromotive force (voltage V0) of the main pump controlling oxygen partial pressure detection sensor cell 80. Further, the pump current Ip0 is controlled by feedback-controlling the pump voltage Vp0 of a variable power supply 24 so as to make the voltage V0 the target value. Consequently, the oxygen concentration in the first internal cavity 20 can be maintained at a predetermined constant value.

The third diffusion control section 30 is a part which gives predetermined diffusion resistance to the gas to be measured, the oxygen concentration (oxygen partial pressure) of the gas having been controlled by the operation of the main pump cell 21 in the first internal cavity 20, and leads the gas to be measured into the second internal cavity 40.

The second internal cavity 40 is provided as a space for performing a treatment related to the measurement of the nitrogen oxide (NOx) concentration in the gas to be measured that is introduced through the third diffusion control section 30. The NOx concentration is measured mainly in the second internal cavity 40 in which the oxygen concentration is adjusted by an auxiliary pump cell 50 and further the NOx concentration is measured by the operation of a measurement pump cell 41.

In the second internal cavity 40, the gas to be measured is further subjected to adjustment of the oxygen partial pressure by the auxiliary pump cell 50, the gas to be measured having been subjected to adjustment of the oxygen concentration (oxygen partial pressure) in the first internal cavity 20 in advance and, thereafter, having been introduced through the third diffusion control section 30. Consequently, the oxygen concentration in the second internal cavity 40 can be maintained constant with high accuracy and, therefore, the gas sensor 100 can measure the NOx concentration with high accuracy.

The auxiliary pump cell 50 is an auxiliary electrochemical pump cell constructed by an auxiliary pump electrode 51 having a ceiling electrode section 51a provided on an almost entire surface of the lower surface of the second solid electrolyte layer 6 facing the second internal cavity 40, an outer pump electrode 23 (not limited to the outer pump electrode 23, and the element body 101a and an appropriate outside electrode will suffice), and the second solid electrolyte layer 6.

The above-described auxiliary pump electrode 51 is arranged in the second internal cavity 40 so as to have a similar tunnel-like structure to the above-described inner pump electrode 22 disposed in the first internal cavity 20. That is, a tunnel-like structure is constructed, in which the ceiling electrode section 51a is formed on the second solid electrolyte layer 6 providing the ceiling surface of the second internal cavity 40, a bottom electrode 51b is formed on the first solid electrolyte layer 4 providing the bottom surface of the second internal cavity 40, and then, side electrode portions (not shown in the drawing) for connecting the ceiling electrode section 51a to the bottom electrode 51b are formed on both side wall surfaces of the spacer layer 5 providing side walls of the second internal cavity 40. In this regard, the auxiliary pump electrode 51 is formed by using a material having weakened ability to reduce NOx components in the gas to be measured in the same manner as the inner pump electrode 22.

In the auxiliary pump cell 50, oxygen in the atmosphere in the second internal cavity 40 can be pumped out to the outside space or oxygen in the outside space can be pumped into the second internal cavity 40 by applying a predetermined pump voltage Vp1 between the auxiliary pump electrode 51 and the outer pump electrode 23.

In addition, in order to control the oxygen partial pressure in the atmosphere in the second internal cavity 40, an electrochemical sensor cell, that is, an auxiliary pump controlling oxygen partial pressure detection sensor cell 81 is constructed by the auxiliary pump electrode 51, the reference electrode 42, the second solid electrolyte layer 6, the spacer layer 5, the first solid electrolyte layer 4, and the third substrate layer 3.

In this regard, the auxiliary pump cell 50 performs pumping by a variable power supply 52 which is voltage-controlled on the basis of the electromotive force (voltage V1) detected by the auxiliary pump controlling oxygen partial pressure detection sensor cell 81. Consequently, the oxygen partial pressure in the atmosphere in the second internal cavity 40 is controlled to a low partial pressure that does not substantially affect the measurement of NOx.

In addition to this, the pump current Ip1 thereof is used for controlling the electromotive force of the main pump controlling oxygen partial pressure detection sensor cell 80. Specifically, the pump current Ip1 serving as a control signal is input into the main pump controlling oxygen partial pressure detection sensor cell 80, and by controlling the above described target value of the voltage V0 thereof the gradient of the oxygen partial pressure in the gas to be measured, which is introduced from the third diffusion control section 30 into the second internal cavity is controlled so as to be always constant. In the case of application as a NOx sensor, the oxygen concentration in the second internal cavity 40 is maintained at a constant value of about 0.001 ppm by the functions of the main pump cell 21 and the auxiliary pump cell 50.

The measurement pump cell 41 measures the NOx concentration in the gas to be measured in the second internal cavity 40. The measurement pump cell 41 is an electrochemical pump cell constructed by a measurement electrode 44 disposed on the upper surface of the first solid electrolyte layer 4 facing the second internal cavity and at the position apart from the third diffusion control section 30, the outer pump electrode 23, the second solid electrolyte layer 6, the spacer layer 5, and the first solid electrolyte layer 4.

The measurement electrode 44 is a porous cermet electrode. The measurement electrode 44 also functions as a NOx reduction catalyst for reducing NOx present in the atmosphere in the second internal cavity 40. Further, the measurement electrode 44 is covered with a fourth diffusion control section 45.

The fourth diffusion control section 45 is a film composed of a ceramic porous body. The fourth diffusion control section 45 has a function of restricting the amount of NOx flowing into the measurement electrode 44 and, in addition, a function as a protective film for the measurement electrode 44. In the measurement pump cell 41, oxygen generated by decomposition of nitrogen oxides in the atmosphere around the measurement electrode 44 is pumped out and the amount of generation thereof can be detected as a pump current Ip2.

Also, in order to detect the oxygen partial pressure around the measurement electrode 44, an electrochemical sensor cell, that is, a measurement pump controlling oxygen partial pressure detection sensor cell 82 is constructed by the first solid electrolyte layer 4, the third substrate layer 3, the measurement electrode 44, and the reference electrode 42. A variable power supply 46 is controlled on the basis of the electromotive force (voltage V2) detected by the measurement pump controlling oxygen partial pressure detection sensor cell 82.

The gas to be measured, which is introduced into the second internal cavity 40, reaches the measurement electrode 44 through the fourth diffusion control section 45 under circumstances where the oxygen partial pressure is controlled. Nitrogen oxides in the gas to be measured around the measurement electrode 44 are reduced ($2NO \rightarrow N_2+O_2$) and oxygen is generated. Then, the resulting oxygen is pumped by the measurement pump cell 41. At that time, the voltage Vp2 of the variable power supply 46 is controlled so as to make the control voltage V2 detected by the measurement pump controlling oxygen partial pressure detection sensor cell 82 constant (target value). The amount of oxygen generated around the measurement electrode 44 is proportional to the concentration of the nitrogen oxides in the gas to be measured and, therefore, the nitrogen oxide concentration in the gas to be measured is calculated by using the pump current Ip2 in the measurement pump cell 41.

In addition, in the case where the measurement electrode 44, the first solid electrolyte layer 4, the third substrate layer 3, and the reference electrode 42 are combined so as to constitute an oxygen partial pressure detection device as an electrochemical sensor cell, the electromotive force in accordance with the difference between the amount of oxygen generated by reduction of NOx components in the atmosphere around the measurement electrode 44 and the amount of oxygen contained in the reference air can be detected and, thereby, the concentration of NOx components in the gas to be measured can be determined.

Further, a sensor cell 83 is constructed by the second solid electrolyte layer 6, the spacer layer 5, the first solid electrolyte layer 4, the third substrate layer 3, the outer pump electrode 23, and the reference electrode 42. The oxygen partial pressure in the gas to be measured in the outside of the sensor can be detected by the electromotive force (voltage Vref) obtained by the sensor cell 83.

In the gas sensor 100 having the above-described configuration, the gas to be measured, which has an oxygen partial pressure always maintained at a low constant value (value that does not substantially affect the measurement of NOx) by actuation of the main pump cell 21 and the auxiliary pump cell 50, is fed to the measurement pump cell 41. Therefore, the NOx concentration in the gas to be measured can be determined on the basis of the pump current Ip2 that flows because oxygen, which is generated by reduction of NOx nearly in proportion to the NOx concentration in the gas to be measured, is pumped out of the measurement pump cell 41.

Further, in order to enhance the oxygen ion conductivity of the solid electrolyte, the element body 101a includes a heater unit 70 having a function of adjusting the temperature including heating the element body 101a and keeping the temperature. The heater unit 70 includes a heater connector electrode 71, a heater 72, a through hole 73, a heater insulating layer 74, and a pressure release hole 75.

The heater connector electrode 71 is an electrode formed so as to contact with the lower surface of the first substrate layer 1. The electric power can be supplied from the outside to the heater unit 70 by connecting the heater connector electrode 71 to an external power supply.

The heater 72 is an electric resistor formed to be sandwiched between the second substrate layer 2 and the third substrate layer 3 in the vertical direction. The heater 72 is connected to the heater connector electrode 71 through the through hole 73 and generates heat by being supplied with an electric power from the outside through the heater connector electrode 71 so as to heat the solid electrolyte constituting the element body 101a and keep the temperature.

Also, the heater 72 is embedded over an entire range from the first internal cavity 20 to the second internal cavity 40 and the entirety of the element body 101a can be adjusted to have a temperature at which the above-described solid electrolyte is activated.

The heater insulating layer 74 is an insulating layer formed on the upper and lower surfaces of the heater 72 by using an insulator, e.g., alumina. The heater insulating layer 74 is formed for the purpose of establishing electrical insulation between the second substrate layer 2 and the heater 72 and electrical insulation between the third substrate layer 3 and the heater 72.

The pressure release hole 75 is a part provided so as to penetrate the third substrate layer 3 and atmosphere introducing layer 48 and communicate with the reference gas introduction space 43 and is formed for the purpose of reducing an internal pressure increase associated with a temperature increase in the heater insulating layer 74.

As shown in FIGS. 1 to 3, the element body 101a is partially covered with the porous protective layer 90. The porous protective layer 90 includes five porous protective layers 90a to 90e formed on respective five of the six surfaces of the element body 101a. The porous protective layer 90a covers part of the upper surface of the element body 101a. The porous protective layer 90b covers part of the lower surface of the element body 101a. The porous protective layer 90c covers part of the left surface of the element body 101a. The porous protective layer 90d covers part of the right surface of the element body 101a. The porous protective layer 90e covers the entire forward end surface of the element body 101a. Each of the porous protective layer 90a to 90d covers the entire region of the corresponding surface of the element body 101a that extends rearward a distance L from the forward end surface of the element body 101a (see FIG. 2). The porous protective layer 90a also covers a portion in which the outer pump electrode 23 is formed. The porous protective layer 90e also covers the gas inlet 10. However, since the porous protective layer 90e is a porous body, the measurement-object gas can flow through the porous protective layer 90e and reach the gas inlet 10. The porous protective layer 90 covers part of the element body 101a (its part including the forward end surface of the element body 101a and extending the distance L from the forward end surface) to protect the covered portion. The porous protective layer 90 plays a role, for example, in preventing the occurrence of cracking in the element body 101a due to adhesion of moisture etc. in the measurement-object gas. The distance L is defined within the range of (0<distance L<the longitudinal length of the element body 101a) based on the range of the element body 101a of the gas sensor 100 that is to be exposed to the measurement-object gas or based on the position of the outer pump electrode 23. In the present embodiment, the distance L is longer than the length of the measurement-object gas flow portion 9 in the forward-rearward direction. Therefore, the rear end of the porous protective layer 90 is located rearward of the rear end of the measurement-object gas flow portion 9.

Each of the porous protective layers 90a to 90e has a two-layer structure. The porous protective layer 90a includes an outer protective layer 91a and an inner protective layer 92a. The inner protective layer 92a covers part of the upper surface of the element body 101a. The outer protective layer 91a is disposed on the outer side of the inner protective layer 92a (the side farther than the inner protective layer 92a when viewed from the element body 101a) and is stacked on the upper side of the inner protective layer 92a. Similarly, the porous protective layer 90b includes an outer protective layer 91b and an inner protective layer 92b. The porous protective layer 90c includes an outer protective layer 91c and an inner protective layer 92c. The porous protective layer 90d includes an outer protective layer 91d and an inner protective layer 92d. The porous protective layer 90e includes an outer protective layer 91e and an inner protective layer 92e. Among the outer protective layers 91a to 91e, adjacent layers are connected to one another. The outer protective layers 91a to 91e are collectively referred to as an outer protective layer 91. Among the inner protective layers 92a to 92e, adjacent layers are connected to one another. The inner protective layers 92a to 92e are collectively referred to as an inner protective layer 92.

As shown in FIG. 3, the inner protective layers 92a to 92d cover the respective four surfaces, i.e., the upper, lower, left, and right surfaces, of the element body 101a that extend in the longitudinal direction (the forward-rearward direction in this case). The inner protective layer 92a covers a portion of the upper surface of the element body 101a that extends the distance L from the forward end as shown in FIG. 2. As shown in FIG. 3, the inner protective layer 92a covers the upper surface of the element body 101a so as to extend from the left end toward the right end. As described above, the distance L is longer than the length of the measurement-object gas flow portion 9 in the forward-rearward direction. Therefore, as shown in FIGS. 3 and 4, the inner protective layer 92a covers the entire portion of a region 102a of the upper surface of the element body 101a that is a projection of the measurement-object gas flow portion 9 onto the upper surface. Similarly, the inner protective layer 92b covers the entire portion of a region 102b of the lower surface of the element body 101a that is a projection of the measurement-object gas flow portion 9 onto the lower surface. The inner protective layer 92c covers the entire portion of a region 102c of the left surface of the element body 101a that is a projection of the measurement-object gas flow portion 9 onto the left surface. The inner protective layer 92d covers the entire portion of a region 102d of the right surface of the element body 101a that is a projection of the measurement-object gas flow portion 9 onto the right surface.

As shown in FIG. 3, in the present embodiment, among the upper, lower, left, and right surfaces of the element body 101a, the upper surface is closest to the measurement-object gas flow portion 9. Specifically, among the upper, lower, left, and right surfaces of the element body 101a, the upper surface is a closest surface closest to the measurement-object gas flow portion 9. The inner protective layer 92a covers this closest surface.

The porous protective layer 90 (outer protective layer 91 and inner protective layer 92) is a porous body and, for example, is formed of a ceramic that contains ceramic particles as constituent particles. Examples of the ceramic particles include particles of metal oxides such as alumina ($Al_2O_3$), zirconia ($ZrO_2$), spinel ($MgAl_2O_4$), and mullite ($Al_6O_{13}Si_2$). The porous protective layer 90 preferably contains at least one of these particles. In this embodiment, the porous protective layer 90 is formed of an alumina porous body.

The porous protective layer 90a includes the inner protective layer 92a and the outer protective layer 91a that is located outward of the inner protective layer 92a and has a smaller porosity than the inner protective layer 92a. In this case, since the porosity P1 of the outer protective layer 91a is small, moisture does not easily pass through the outer protective layer 91a. Since the porosity P2 of the inner protective layer 92a is large, its heat insulating ability is high. In this case, the degree of cooling of the upper side of the element body 101a is reduced, and the waterproofing performance of the sensor element 101 is improved. Similarly, the porous protective layers 90b to have the inner protective layers 92b to 92e, respectively, and the outer protective layers 91b to 91e, respectively, that are located outward of the inner protective layers 92b to 92e and have a smaller porosity than the inner protective layers 92b to 92e. In this case, the degree of cooling of the lower, left, right, and forward sides of the element body 101a that correspond to the porous protective layers 90b to 90e is reduced, and the waterproofing performance of the sensor element 101 is improved.

The porosity P1 of at least one of the outer protective layers 91a to 91e may be 10% or more. When the porosity P1 is 10% or more, the measurement-object gas can sufficiently pass through the outer protective layer 91. Preferably, the porosity P1 of at least one of the outer protective layers 91a to 91e is 60% or less. When the porosity P1 is 60% or less, moisture does not easily pass through the outer protective layer 91. Preferably, the porosity P2 of at least one of the inner protective layers 92a to 92e is 40% or more. When the porosity P2 is 40% or more, the heat insulating effect of the inner protective layer 92 between the outer protective layer 91 and the element body 101a is prevented from becoming insufficient. Preferably, the porosity P2 of at least one of the inner protective layers 92a to 92e is 70% or less. When the porosity P2 is 70% or less, the strength of the inner protective layer 92 is prevented from becoming insufficient.

In the inner protective layer 92a, the standard deviation $\sigma$ of the porosity P2 is 2.3% or less. When the standard deviation of the porosity P2 is 2.3% or less, the volume of partial portions whose porosity is small, i.e., partial portions whose heat insulating ability is low, in the inner protective layer 92a is small, so that the waterproofing performance of the sensor element 101 is improved. Similarly, in each of the inner protective layers 92b to 92e, the standard deviation $\sigma$ of the porosity P2 is 2.3% or less. Preferably, the standard deviation $\sigma$ in at least one of the inner protective layers 92a to 92e is 1.5% or less. The lower limit of the standard deviation $\sigma$ may be equal to the manufacturing lower limit (for example, 0.5% or more).

Preferably, the thickness T1 of at least one of the outer protective layers 91a to 91e is 100 μm or more. When the thickness T1 is 100 μm or more, moisture does not easily pass through the outer protective layer 91. Preferably, the thickness T1 of at least one of the outer protective layers 91a to 91e is 300 μm or less. When the thickness T1 is 300 μm or less, the heat capacity of the outer protective layer 91 is not excessively large, so that an increase in the amount of electric power applied to the heater 72 when the element body 101a is heated can be prevented. Preferably, the thickness T2 of at least one of the inner protective layers 92a to 92e is 300 μm or more. When the thickness T2 is 300 μm or more, the distance between the element body 101a and the outer protective layer 91 is relatively large, and the degree of cooling of the element body 101a is reduced, so that the waterproofing performance is improved. Preferably, the thickness T2 of at least one of the inner protective layers 92a to 92e is 700 μm or less. When the thickness T2 is 700 μm or less, the porous protective layer is prevented from interfering with a protective cover that covers the sensor element 101.

The porosity P2 of the inner protective layer 92a and its standard deviation $\sigma$ are values derived from an image (SEM image) observed and obtained using a scanning electron microscope (SEM) as follows. First, the sensor element 101 is cut in the thickness direction of the inner protective layer 92a such that a cross section of the inner protective layer 92a is used as the observation surface. The cut section in this case is a surface that is parallel to the longitudinal direction of the sensor element 101 and passes through the center of the measurement-object gas flow portion 9 (the left-right center of the measurement-object gas flow portion 9 in this case). Specifically, the cut section used is a cross section taken along C-C in FIG. 3 (a cross section shown in FIG. 4). Therefore, the cut section is a cross section including a portion of the inner protective layer 92a that is located directly above the measurement-object gas flow portion 9, i.e., a cross section including a portion of the inner protective layer 92a that covers the region 102a. The cut section is embedded in a resin and polished to prepare an observation sample. Next, with the magnification of the SEM set to 1000×, an image of the observation surface of the observation sample is taken to obtain an SEM image of the inner protective layer 92a. Next, as shown in FIG. 4, eight observation regions 93a used as regions for porosity computation are defined in the inner protective layer 92a in the SEM image obtained. Each of the observation regions 93a is a substantially rectangular region with (a length of 1 mm)×(the thickness of the inner protective layer 92a). The positions of the eight observation regions 93a are determined such that the eight observation regions 93a are arranged at regular intervals in a portion between the forward and rear ends of the region 102a (see FIG. 4). Then the porosity in each of the eight observation regions 93a in the SEM image is computed using image analysis. Specifically, first, for pixels in one of the observation regions 93a in the SEM image, the luminance distribution in the data about the luminances of the pixels is used to determine a threshold value using a discriminant analysis method (Otsu's method). Then, based on the determined threshold value, the pixels in the image of the one observation region 93a are classified into material and pore portions by binarization, and the area of the material portions and the area of the pore portions are computed. Then the ratio of the area of the pore portions to the total area (the total area of the material portions and the pore portions) is computed as the porosity of the observation region 93a. The porosity of each of the eight observation regions 93a is computed in the same manner. The average of the computed eight porosity values is used as the porosity P2 of the inner protective layer 92a, and the standard deviation of the eight porosity values is used as the standard deviation $\sigma$ in the inner protective layer 92a. For the same inner protective layer 92a, the number of observation regions 93a was changed, and the standard deviation $\sigma$ was computed. Then it was found that, when the number of observation regions 93a was 8 or more, the standard deviations $\sigma$ were substantially the same. It can therefore be inferred that, when the number of observation regions 93a is 8, the standard deviation $\sigma$ can be computed with sufficient accuracy.

The porosity P2 of each of the inner protective layers 92b to 92d and the standard deviation $\sigma$ of the porosity P2 are values computed using the same method as described above. For example, eight observation regions for computing the porosity P2 of the inner protective layer 92b and the standard deviation $\sigma$ of the porosity P2 are substantially rectangular observation regions with (a length of 1 mm)×(the thickness of the inner protective layer 92b), and the positions of these eight observation regions are determined such that the observation regions are arranged at regular intervals in a portion between the forward and rear ends of the region 102b. As for the inner protective layer 92e, since the region of the forward surface of the element body 101a onto which the measurement-object gas flow portion 9 is projected is smaller than the regions 102a to 102d, the observation regions are determined in the entire portion covering the forward surface of the element body 101a in the SEM image of the cross section of the inner protective layer 92e. Specifically, first, a surface parallel to the longitudinal direction of the sensor element 101 and passing through the center of the measurement-object gas flow portion 9 is used as the observation surface. More specifically, the observation surface is a surface parallel to the longitudinal direction and passing through the left-right center of the region 102a of the closest surface of the element body 101a, as in the case of the observation surface of the inner protective layer 92a shown in FIG. 4. Next, in the observation surface of the SEM image, eight observation regions 93e are determined in the portion of the inner protective layer 92e that covers the forward surface of the element body 101a. In the present embodiment, since the upward-downward length of the forward surface of the element body 101a is less than 8 mm, the length of one observation region 93a is not 1 mm. In the SEM image shown in FIG. 4, the portion of the inner protective layer 92e that covers the forward surface of the element body 101a is divided into eight equal parts to determine the eight observation regions 93e. The value of the porosity P1 of each of the outer protective layers 91a to 91e is computed as the average of the porosity values of eight observation regions, as in the case of the porosity P2 of each of the inner protective layers 92a to 92e.

The reason that the standard deviations $\sigma$ in the inner protective layers 92a to 92d are computed in their cross sections covering the respective regions 102a to 102d is as follows. The strength of portions of the element body 101a that are located between the measurement-object gas flow portion 9 and the regions 102a to 102d is low, and these portions are relatively vulnerable to thermal shock. Therefore, reducing the standard deviations $\sigma$ in the portions of the inner protective layer 92 that cover these weak portions largely contributes to the improvement in the waterproofing performance of the sensor element 101. Thus, the standard deviations σ computed in the cross sections of the portions of the inner protective layers 92a to 92d that cover the regions 102a to 102d are used as the standard deviations σ of the inner protective layers 92a to 92d. Similarly, since the strength of a portion of the element body 101a that is located around the gas inlet 10 is low, this portion is relatively vulnerable to thermal shock. Therefore, the value of the standard deviation σ in the inner protective layer 92e is computed using, as the observation surface of the inner protective layer 92e, the cross section cut along the center of the measurement-object gas flow portion 9 as described above.

In this embodiment, the thickness T1 of the outer protective layer 91a and the thickness T2 of the inner protective layer 92a are values determined as follows. First, a SEM image is acquired as in the description above in which a section of the porous protective layer 90a is used as an observation surface, and the boundary between the outer protective layer 91a and the inner protective layer 92a is identified by using the SEM image. A direction perpendicular to the surface (in this case, the upper surface) of the second solid electrolyte layer 6) of the element body 101a on which the porous protective layer 90a is formed is specified as the thickness direction. Then the distance from the surface (the upper surface in this case) of the porous protective layer 90a to the boundary in the thickness direction is derived as the thickness T1. The distance from the surface of the element body 101a to the boundary in the thickness direction is derived as the thickness T2. The thickness T1 and the thickness T2 of each of the porous protective layers 90b to 90e are also values derived through the same procedure.

In this embodiment, the values of the porosity P1 and thickness T1 are set to be the same among the outer protective layers 91a to 91e. Similarly, the values of the porosity P2, the standard deviation σ and the thickness T2 are set to be the same among the inner protective layers 92a to 92e.

Next, a method for manufacturing this gas sensor 100 is described. In the method for manufacturing the gas sensor 100, the element body 101a is first manufactured and then the porous protective layer 90 is formed on the element body 101a to manufacture the sensor element 101.

The method for manufacturing the element body 101a is first described. First, six unfired ceramic green sheets are prepared. Then patterns for electrodes, insulating layers, resistance heating elements, and the like are printed on the ceramic green sheets respectively corresponding to the first substrate layer 1, the second substrate layer 2, the third substrate layer 3, the first solid electrolyte layer 4, the spacer layer 5, and the second solid electrolyte layer 6. Upon completion of formation of the various patterns, the green sheets are dried. Subsequently, the dried sheets are stacked to form a stack. The stack obtained as such includes plural element bodies 101a. The stack is diced into pieces with a size of the element body 101a, and the pieces are fired at a particular temperature to obtain the element bodies 101a.

Figure 5:
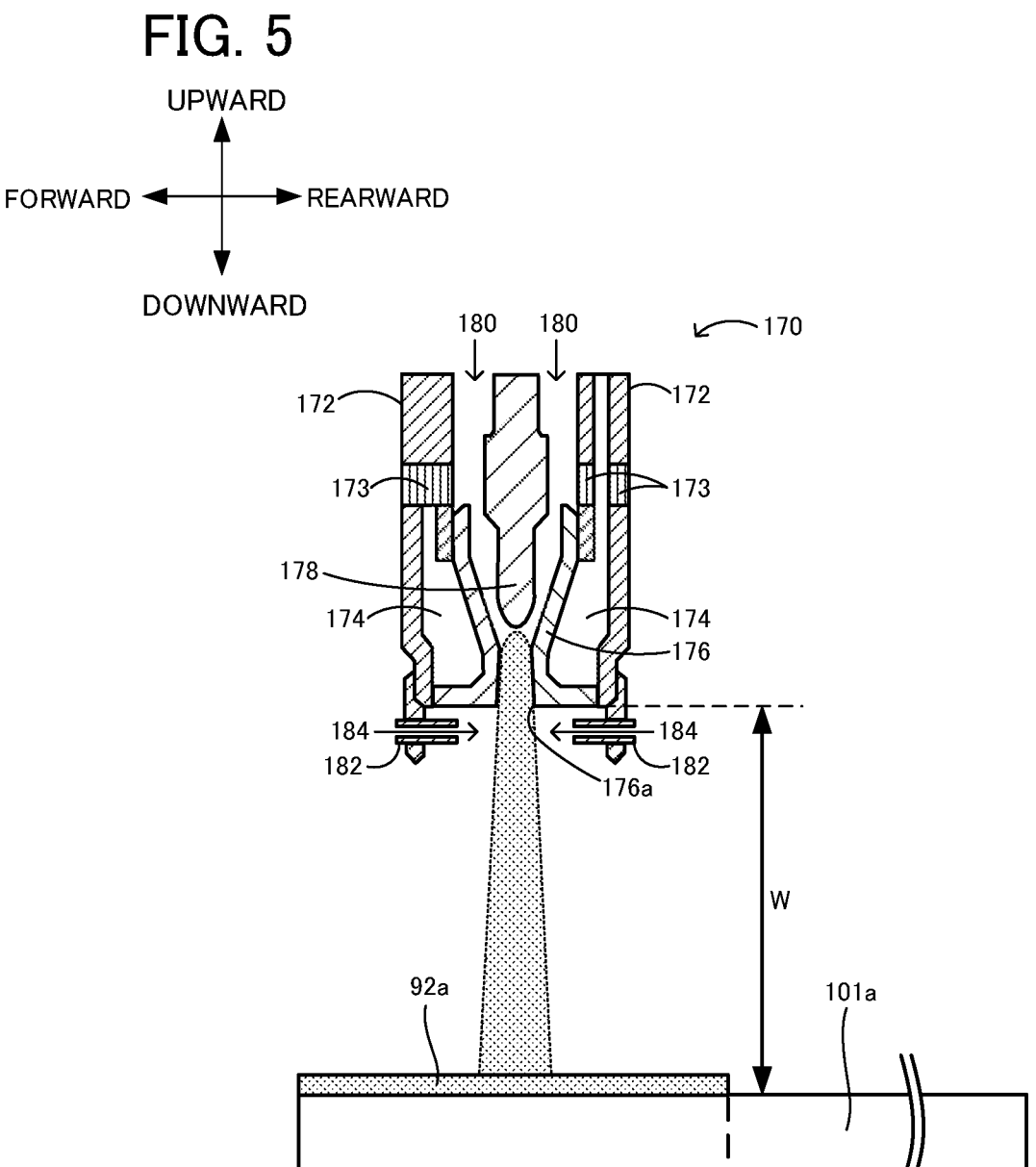
FIG. 5 is an illustration of plasma spraying using a plasma gun 170.

Next, a method for forming the porous protective layer 90 on the element body 101a will be described. In the present embodiment, the inner protective layers 92a to 92e and the outer protective layers 91a to 91e are formed one by one by plasma spraying. FIG. 5 is an illustration of the plasma spraying using a plasma gun 170. In the example shown in FIG. 5, the manner of forming the inner protective layer 92a is shown, and a cross section of the plasma gun 170 is shown. The plasma gun 170 includes an anode 176 and a cathode 178 that are electrodes for generating plasma and further includes a substantially cylindrical outer circumferential portion 172. The outer circumferential portion 172 includes an insulating portion (insulator) 173 for insulation from the anode 176. A powder supply portion 182 for supplying a powder spray material 184 that is the material forming the porous protective layer 90 is formed at the lower end of the outer circumferential portion 172. A water cooling jacket 174 is provided between the outer circumferential portion 172 and the anode 176, and the anode 176 can thereby be cooled. The anode 176 is formed into a tubular shape and has a nozzle 176a having a downward opening. A plasma-generating gas 180 is supplied between the anode 176 and the cathode 178 from above.

When the inner protective layer 92a is formed, a voltage is applied between the anode 176 and the cathode 178 of the plasma gun 170 to generate an arc discharge in the presence of the plasma-generating gas 180 supplied, and the plasma-generating gas 180 is converted into a high-temperature plasma state. The gas in the plasma state is injected from the nozzle 176a as a high-temperature high-speed plasma jet. The powder spray material 184 and a carrier gas are supplied from the powder supply portion 182. In this manner, the powder spray material 184 is heated, melted, and accelerated by the plasma and then impinges on the surface (upper surface) of the element body 101a. The powder spray material 184 is thereby rapidly solidified, and the inner protective layer 92a is formed.

The plasma-generating gas 180 used may be, for example, in inert gas such as argon gas. The flow rate of the argon gas is, for example, 40 to 50 L/min, and its supply pressure is, for example, 0.5 to 0.6 MPa. The voltage applied between the anode 176 and the cathode 178 is, for example, a DC voltage of 80 to 90 V, and the current is, for example, 300 to 400 A.

The powder spray material 184 contains a raw material powder used as the raw material of the porous protective layer 90 described above. In the present embodiment, the raw material powder is alumina powder. The particle diameter of the raw material powder is, for example, 1 μm to 50 μm and is more preferably 20 μm to 30 μm. The carrier gas used to supply the powder spray material 184 may be, for example, the same argon gas as the plasma-generating gas 180. The flow rate of the carrier gas is, for example, 3 to 5 L/min, and the supply pressure is, for example, 0.5 to 0.6 MPa.

When the plasma spraying is performed, it is preferable that the distance W between the nozzle 176a that is the outlet for the plasma gas in the plasma gun 170 and a surface of the element body 101a on which the inner protective layer 92a is to be formed (the upper surface of the element body 101a in FIG. 5) is set to 150 mm to 200 mm. The plasma spraying may be performed while the plasma gun 170 is moved appropriately (moved in the left-right direction in FIG. 5) according to the formation area of the porous protective layer 90. Even in this case, it is preferable to maintain the distance W within the above range.

The inner protective layers 92b to 92e are also formed one by one in the same manner except that they are formed on different surfaces of the element body 101a. After the formation of the inner protective layers 92 (the inner protective layers 92a to 92e), the outer protective layers 91a to 91e are formed one by one using plasma spraying in the same manner as described above. The plasma spraying is performed, for example, in an air atmosphere at room temperature. In this manner, the inner protective layer 92 (the inner protective layers 92a to 92e) and the outer protective layer 91 (the outer protective layers 91a to 91e) are formed on the upper, lower, left, and right surfaces and the forward end surface of the element body 101a, and the porous protective layer 90 is thereby formed. When the porous protective layer 90 is formed on part of the surface of the element body 101a (on a region extending the distance L from the forward end toward the rear end) as in the case of the porous protective layer 90a to the porous protective layer 90d, a region on which the porous protective layer 90 is not formed may be covered with a mask.

When the porous protective layer 90 is formed using the plasma spraying as described above, a pore forming material may be added to the powder spray material 184. The porosities P1 and P2 in the porous protective layer 90 can be controlled by adjusting the mixing ratio of the pore forming material. The pore forming material used may be a material that disappears when heated. Examples of the pore forming material include theobromine and acrylic resins. The pore forming material contained in the powder spray material 184 for the inner protective layer 92 may be sieved in advance through a sieve with a prescribed mesh size to reduce variations in the particle diameter of the pore forming material. In this manner, the standard deviation $\sigma$ of the porosity of the inner protective layer 92 can be reduced. When the powder spray material 184 contains the pore forming material, the element body 101a after the plasma spraying is subjected to heat treatment. The pore forming material thereby disappears, and pores are formed in the porous protective layer 90. The thickness T1 and the thickness T2 can be controlled by increasing or decreasing the plasma spraying time.

The porous protective layer 90 is formed on the element body 101a in the manner described above, and the sensor element 101 is thereby obtained. Then a gas sensor 100 with the sensor element 101 installed therein is produced. For example, an element sealing member is attached to the sensor element 101 and then sealed and fixed, and a connector and lead wires are attached to the rear end side of the sensor element 101. A protection cover is attached to the forward end side of the sensor element 101 in the element sealing member. An outer tube is attached to the rear end side of the sensor element 101 in the element sealing member, and the lead wires are drawn out from the outer tube. The process for assembling the gas sensor 100 by installing the sensor element 101 as described above is well-known and described in, for example, Japanese Unexamined Patent Application Publication No. 2015-178988.

During the use of the thus-produced gas sensor 100, the measurement-object gas flows into the protection cover of the gas sensor 100, reaches the sensor element 101, passes through the porous protective layer 90, and flows into the gas inlet 10. The sensor element 101 detects the concentration of NOx in the measurement-object gas flowing into the gas inlet 10. In this case, moisture contained in the measurement-object gas also enters the inside of the protection cover and may adhere to the surface of the porous protective layer 90. As described above, the temperature of the element body 101a is adjusted by the heater 72 to a temperature (e.g., 800° C.) at which the solid electrolyte is activated. Generally, when moisture adheres to the sensor element 101, the temperature on the outer side of the element body 101a decreases rapidly. In this case, the temperature gradient between the inner side of the element body 101a and the outer side of the element body 101a becomes large, and this may cause cracking in the element body 101a. As described above, in the porous protective layer 90 in the present embodiment, the porosity P1 of the outer protective layer 91 is smaller than the porosity P2 of the inner protective layer 92. Therefore, since the porosity P1 of the outer protective layer 91 is small, moisture does not easily pass through the outer protective layer 91. Since the porosity P2 of the inner protective layer 92 is large, its heat insulating ability is high. The waterproofing performance of the sensor element 101 is thereby improved. Moreover, in the inner protective layer 92 in the present embodiment, the standard deviation $\sigma$ of the porosity P2 is 2.3% or less, and the variations in the porosity are small. Since the standard deviation $\sigma$ of the porosity in the inner protective layer 92 is 2.3% or less, the volume of partial portions whose porosity is small, i.e., partial portions whose heat insulating ability is low, in the inner protective layer 92 is small, and the degree of cooling of the element body 101a when moisture adheres to the sensor element 101 is reduced. Therefore, the waterproofing performance of the sensor element 101 in the present embodiment is further improved as compared with that of, for example, a sensor element including, instead of the inner protective layer 92, an inner protective layer that has the same porosity but in which the standard deviation $\sigma$ is larger.

In the sensor element 101 in the present embodiment described above in detail, the standard deviation of the porosity in the porous protective layer 90 (particularly in the inner protective layer 92) is 2.3% or less, and the waterproofing performance of the sensor element 101 is thereby improved.

The porous protective layer 90 includes the inner protective layer 92 and the outer protective layer 91 located outward of the inner protective layer 92 and having a smaller porosity than the inner protective layer 92. In the porous protective layer 90, the standard deviation $\sigma$ of the porosity in the inner protective layer 92 is 2.3% or less. In this case, since the porosity P1 of the outer protective layer 91 is small, moisture does not easily pass through the outer protective layer 91. Since the porosity P2 of the inner protective layer 92 is large, its heat insulating ability is high, and the waterproofing performance of the sensor element 101 is thereby improved. Moreover, since the standard deviation $\sigma$ of the porosity P2 in the inner protective layer 92 is 2.3% or less, the volume of partial portions whose porosity is small, i.e., partial portions whose heat insulating ability is low, in the inner protective layer 92 is small, so that the waterproofing performance of the sensor element 101 is further improved.

Moreover, the element body 101a has the elongate rectangular parallelepiped shape, and the measurement-object gas flow portion 9 through which the measurement-object gas introduced flows is disposed inside the element body 101a. The inner protective layer 92a in the inner protective layer 92 covers the closest surface (the upper surface in this case) that is closest to the measurement-object gas flow portion 9 among the four surfaces (the upper, lower, left, and right surfaces) of the element body 101a that extend in the longitudinal direction. In the inner protective layer 92a, the standard deviation $\sigma$ of the porosity in a portion covering the region 102a of the closest surface that is a projection of the measurement-object gas flow portion 9 onto the closest surface is 2.3% or less. As described above, the strength of the portions of the element body 101a that are located between the measurement-object gas flow portion 9 and the regions 102a to 102d is low, and these portions are relatively vulnerable to thermal shock. In particular, the thickness of the portion between the closest surface and the measurement-object gas flow portion (the portion between the region 102a and the measurement-object gas flow portion 9 in this case) is small, and this portion is particularly vulnerable to thermal shock. However, since the standard deviation $\sigma$ of the porosity in the portion of the inner protective layer 92a that covers the region 102a is 2.3% or less, the occurrence of cracking in the portion vulnerable to thermal shock can be reduced, and the waterproofing performance of the sensor element 101 can thereby be improved.

The gas inlet 10 used as the inlet of the measurement-object gas flow portion 9 has an opening on the longitudinal end surface (the forward surface in this case) of the element body 101a. The inner protective layer 92e in the inner protective layer 92 covers the forward surface of the element body 101a, and the standard deviation $\sigma$ of the porosity in the portion covering the forward surface is 2.3% or less. As described above, the strength of the portion of the element body 101a that is located around the gas inlet 10 is low, and this portion is relatively vulnerable to thermal shock. However, the standard deviation $\sigma$ of the porosity in the inner protective layer 92e that is the portion of the inner protective layer 92 that covers the forward surface on which the gas inlet 10 has its opening is 2.3% or less. Therefore, the occurrence of cracking in the portion vulnerable to thermal shock can be reduced, and the waterproofing performance of the sensor element 101 is improved.

When the porosity P2 of the inner protective layer 92 is 40% or more, the heat insulating effect between the outer protective layer 91 and the element body 101a is prevented from becoming insufficient. When the porosity P2 of the inner protective layer 92 is 70% or less, the strength of the inner protective layer 92 is prevented from becoming insufficient.

When the standard deviation $\sigma$ in the inner protective layer 92 is 1.5% or less, the waterproofing performance of the sensor element 101 is further improved.

The present invention is not limited to the embodiment described above. It will be appreciated that the present invention can be implemented in various forms so long as they fall within the technical scope of the invention.

In the embodiment described above, the standard deviation $\sigma$ of the porosity in all the inner protective layers 92a to 92e is 2.3% or less. However, for example, it is only necessary that the standard deviation $\sigma$ in at least one of the inner protective layers 92a to 92e be 2.3% or less. When the standard deviation $\sigma$ in at least one of the inner protective layers 92a to 92e is 2.3% or less, the above-described effects can be obtained for the at least one of the inner protective layers 92a to 92e. However, as for the inner protective layers 92a to 92e, the larger the number of inner protective layers in which the standard deviation $\sigma$ is 2.3% or less, the better. It is more preferable that the standard deviation $\sigma$ in all the inner protective layers 92a to 92e (i.e., the entire inner protective layer 92) is 2.3% or less.

In the embodiment described above, the standard deviation $\sigma$ derived based on the portion of the inner protective layer 92a that covers the region 102a is 2.3% or less. However, it is preferable that, also in portions other than the portion covering the region 102a, the standard deviation $\sigma$ derived using the same method as described above is 2.3% or less. Moreover, the standard deviation $\sigma$ in the portion of the inner protective layer 92a that covers the region 102a may be more than 2.3%. In this case, it is only necessary that the standard deviation $\sigma$ computed in any other part of the cross section of the inner protective layer 92a be 2.3% or less. However, as described above, reducing the standard deviation $\sigma$ in the portion of the inner protective layer 92a that covers the region 102a largely contributes to the improvement in the waterproofing performance. It is therefore preferable that the standard deviation $\sigma$ in at least the portion of the inner protective layer 92a that covers the region 102a is 2.3% or less. The same applies to the inner protective layers 92b to 92e.

In the embodiment described above, each of the porous protective layers 90a to 90e has the two-layer structure, but this is not a limitation. For example, the porous protective layer 90 may further include an additional layer located outward of the outer protective layer 91, may further include an additional layer between the outer protective layer 91 and the inner protective layer 92, or may further include an additional layer on the element body 101a side of the inner protective layer 92. When the porous protective layer 90 has a structure including three or more layers, the "inner protective layer" is any of the layers other than the outermost layer in the porous protective layer 90, and it is only necessary that the standard deviation $\sigma$ of the porosity in this layer be 2.3% or less. Specifically, when the porous protective layer 90 has a structure including three or more layers, it is only necessary that the standard deviation $\sigma$ of the porosity in at least one of the layers in the porous protective layer 90 excluding the outermost layer be 2.3% or less. In this case, the heat insulating effect of the layer (inner protective layer) in which the standard deviation $\sigma$ is 2.3% or less is unlikely to become insufficient. Therefore, the effect of improving the waterproofing performance of the sensor element 101 is obtained, as in the above embodiment. In this case, it is preferable that a layer having a smaller porosity than the layer in which the standard deviation $\sigma$ is 2.3% or less is present on the outer side of this layer, and such a layer is referred to as the "outer protective layer."

Figures 6, 7:
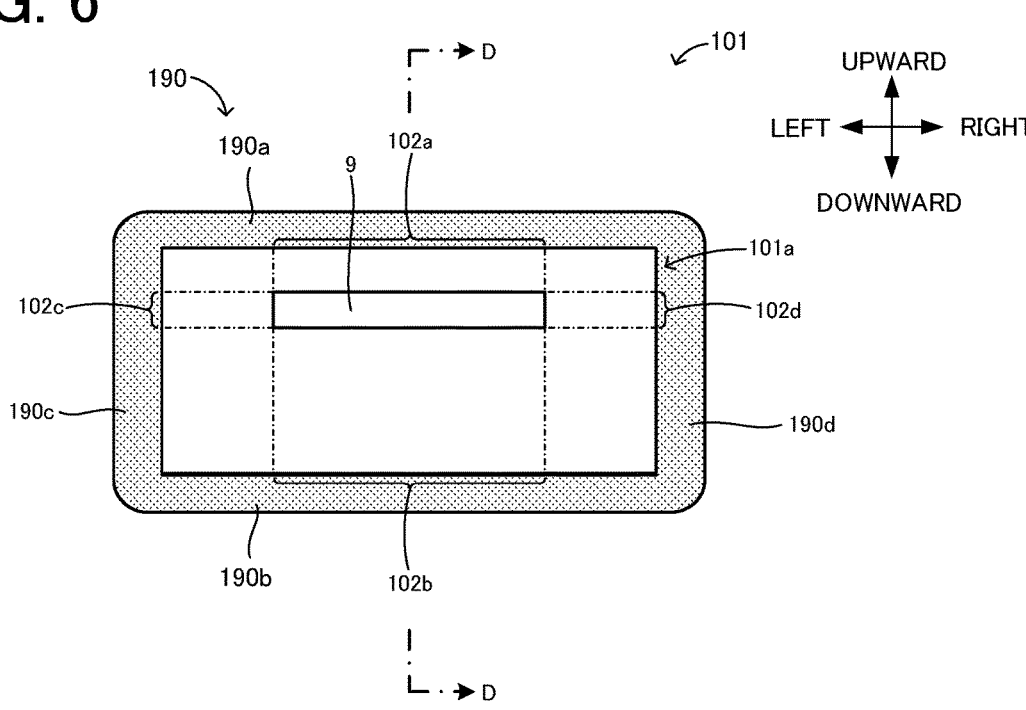
FIG. 6 is a cross-sectional view of a porous protective layer 190 in a modification.
FIG. 7 is a cross-sectional view taken along D-D in FIG. 6.

In the embodiment described above, the porous protective layer 90 includes the outer protective layer 91 and the inner protective layer 92, but the porous protective layer 90 may have a single-layer structure. FIG. 6 is a cross-sectional view of a porous protective layer 190 in a modification. FIG. 7 is a cross-sectional view taken along D-D in FIG. 6. The porous protective layer 190 shown in FIGS. 6 and 7 includes porous protective layers 190a to 190e formed on respective five surfaces of the element body 101a. The porous protective layers 190a to 190e have the same structures as those of the porous protective layers 90a to in the above-described embodiment except that these layers have a single layer structure. Even in this porous protective layer 190, when the standard deviation $\sigma$ of the porosity in at least one of the porous protective layers 190a to 190e is 2.3% or less, the above-described effects can be obtained for the at least one of the porous protective layers 190a to 190e. A method for computing the standard deviation $\sigma$ in the porous protective layers 190a to 190e is the same as the method for computing the standard deviation $\sigma$ in the inner protective layers 92a to 92e described above. It is preferable that, in the porous protective layer 190a in the porous protective layer 190 that covers the above-described closest surface (the upper surface of the element body 101a in this case), the standard deviation $\sigma$ of the porosity in the portion of the porous protective layer 190a that covers the region 102a is 2.3% or less, as in the embodiment described above. Moreover, it is preferable that, in the porous protective layer 190e in the porous protective layer 190 that covers the forward surface of the element body 101a (the surface on which the gas inlet has its opening), the standard deviation $\sigma$ of the porosity in the portion of the porous protective layer 190e that covers the forward surface of the element body 101a is 2.3% or less, as in the embodiment described above.

In the porous protective layer 190 having the single layer structure shown in FIGS. 6 and 7, it is preferable that the porosity of at least one of the porous protective layers 190a to 190*e* is 10% or more. When the porosity is 10% or more, the porous protective layer 190 does not prevent the flow of the measurement-object gas. It is preferable that the porosity of at least one of the porous protective layers 190*a* to 190*e* is 40% or less. When the porosity is 40% or less, moisture does not easily pass through the porous protective layer 190. Preferably, the thickness of at least one of the porous protective layers 190*a* to 190*e* is 100 μm or more. When the thickness is 100 μm or more, the waterproofing performance of the element body 101*a* is prevented from becoming insufficient. Preferably, the thickness of at least one of the porous protective layers 190*a* to 190*e* is 500 μm or less. Since the porous protective layer 190 has the single layer structure, it is necessary that the porosity be smaller than that of the inner protective layer 92 in the above-described embodiment in order to prevent moisture from passing through. Therefore, in the porous protective layer 190 having the single layer structure, it is preferable that the thickness is smaller than that of the inner protective layer in the embodiment described above.

In the embodiment described above, the porous protective layer 90 includes the porous protective layers to 90*e*, but this is not a limitation. It is only necessary that the porous protective layer 90 covers at least part of the element body 101*a*. For example, the porous protective layer 90 may not include at least one of the porous protective layers 90*a* to 90*e*. This also applies to the porous protective layer 190 shown in FIGS. 6 and 7.

In the embodiment described above, the outer protective layer 91 and the inner protective layer 92 are formed of the same ceramic material (alumina), but this is not a limitation. They may be formed of different materials.

In the embodiment described above, the porous protective layer 90 is formed by plasma spraying, but this is not a limitation. For example, the porous protective layer 90 may be formed using screen printing, a mold casting method, or a dipping method. When the porous protective layer 90 is formed using one of these methods, the standard deviation σ of the porosity can be reduced by using a pore forming material with small variations in particle diameter, as in the embodiment described above.

EXAMPLES

Examples in which sensor elements were actually produced will be described. Experimental Examples 1 to 3 correspond to Examples of the present invention, and Experimental Examples 4 to 6 correspond to Comparative Examples. However, the present invention is not limited to the following Examples.

Experimental Example 1

In Experimental Example 1, a sensor element was manufactured by the method for manufacturing the sensor element 101 according to the embodiment described above. First, an element body 101*a* having a length of 67.5 mm in the forward-rearward direction, a width of 4.25 mm in the left/right direction, and a thickness of 1.45 mm in the upward-downward direction illustrated in FIGS. 1 and 2 was made. In making the element body 101*a*, ceramic green sheets were prepared by mixing zirconia particles containing 4 mol % of yttria acting as a stabilizer, an organic binder, and an organic solvent, and forming the resulting mixture by tape casting.

Next, plasma spraying was used to form a porous protective layer 90 to thereby produce a sensor element 101 serving as Experimental Example 1. The porous protective layer 90 in Experimental Example 1 was formed as follows. The plasma gun 170 used was Sinplex Pro-90 manufactured by Oerlikon Metco. The powder spray material 184 used to form the inner protective layer 92 was a mixture of an alumina powder having an average particle diameter of 20 μm and a pore forming material. The pore forming material used had been sieved through a sieve with a prescribed mesh size to reduce variations in the particle diameter of the pore forming material. The plasma-generating gas 180 used was a mixture of argon gas (flow rate: 50 L/min, supply pressure: 0.5 MPa) and hydrogen (flow rate: 10 L/min, supply pressure: 0.5 MPa). The voltage applied between the anode 176 and the cathode 178 was a DC voltage of 70 V. The current was 500 A. The carrier gas used to supply the powder spray material 184 was argon gas (flow rate: 4 L/min, supply pressure: 0.5 MPa). The distance W was set to 150 mm. The plasma spraying was performed in an air atmosphere at room temperature. The direction of thermal spraying from the plasma gun 170 (the direction of the nozzle 176*a*) was perpendicular to the surface of the sensor element 101 on which the inner protective layer 92 was to be formed. The inner protective layer 92 was formed under the conditions described above, and then the outer protective layer 91 was formed. The powder spray material 184 used to form the outer protective layer 91 was the same alumina particles as those used for the inner protective layer 92. The pore forming material was not added to the powder spray material 184, so that the porosity of the outer protective layer 91 was smaller than the porosity of the inner protective layer 92. The plasma spraying conditions were the same as those for the inner protective layer 92. After the formation of the outer protective layer 91, the element body 101*a* was subjected to heat treatment to cause the pore forming material in the inner protective layer 92 to disappear, and the sensor element 101 in Experimental Example 1 was thereby obtained.

Experimental Examples 2 to 6

Sensor elements 101 in Experimental Examples 2 to 6 were produced in the same manner as in Experimental Example 1 except that, while the same outer protective layer 91 as that in Experimental Example 1 was used, the mesh size of the sieve used for the pore forming material for the inner protective layer 92 was appropriately changed to adjust the particle diameter of the pore forming material to thereby change the standard deviation G.

[Derivation of Parameters of Outer Protective Layer and Inner Protective Layer]

For each of Experimental Examples 1 to 6, the porosity P1 of the outer protective layer 91, its thickness T1, the porosity P2 of the inner protective layer 92, the standard deviation σ of the porosity P2 in the inner protective layer 92, and its thickness T2 were derived using the methods described above. In all Experimental Examples 1 to 6, the porosity P1 was 25%, and the thickness T1 was 200 μm. The porosity P2 of the inner protective layer 92 was 55%, and the thickness T2 was 550 μm. The value of the standard deviation σ in each of Experimental Examples 1 to 6 is shown in Table 1. The SEM images were obtained and analyzed using SU1510 manufactured by Hitachi High-Technologies Corporation and Image-Pro Plus 7.0 manufactured by Media Cybernetics. In Experimental Example 1, the values of the porosity P1 and the thickness T1 were the same for all the outer protective layers 91*a* to 91*e*. Similarly, in Experimental Example 1, the values of the porosity P2, the thickness T2, and the standard deviation σ were the same for all the inner protective layers 92a to 92e. Similarly, in each of Experimental Examples 2 to 6, the values of the porosity P1 and the thickness T1 were the same for all the outer protective layers 91a to 91e, and the values of the porosity P2, the thickness T2, and the standard deviation σ were the same for all the inner protective layers 92a to 92e.

[Evaluation of Waterproofing Performance]

For each of the sensor elements in Experimental Examples 1 to 6, the waterproofing performance of the sensor element 101 was evaluated. Specifically, first, the heater 72 was energized to increase the temperature to 800° C., and the element body 101a was thereby heated. With this state maintained, the main pump cell 21, the auxiliary pump cell the main-pump-control oxygen-partial-pressure detection sensor cell 80, the auxiliary-pump-control oxygen-partial-pressure detection sensor cell 81, etc. were operated in an air atmosphere to control the concentration of oxygen in the first internal cavity 20 such that the oxygen concentration was maintained at a constant value. Then, after waiting for pump current Ip0 to stabilize, water was added dropwise onto the porous protective layer 90, and the presence or absence of cracking in the element body 101a was determined based on whether the pump current Ip0 was changed to a value larger than a prescribed threshold value. When cracking occurs in the element body 101a due to thermal shock by the water droplets, oxygen easily flows into the first internal cavity through the cracked portion, so that the value of the pump current Ip0 increases. Therefore, when the pump current Ip0 was larger than the prescribed threshold value determined experimentally, it was determined that cracking had occurred in the element body 101a due to the water droplets. A plurality of tests were performed while the amount of water droplets was gradually increased. The amount of the water droplets at which the cracking occurred for the first time was used as a waterproofing amount [μL]. For each of the sensor elements in Experimental Examples 1 to 6, the average of three measurements obtained in three tests was derived as the waterproofing amount [μL]. The larger the waterproofing amount, the higher the waterproofing performance of the sensor element 101. Among Experimental Examples 1 to 6, the waterproofing amount in Experimental Example 6 was smallest. Therefore, for each of Experimental Examples 1 to 5, the ratio of the waterproofing amount with respect to the waterproofing amount in Experimental Example 6 was computed. For each of the Experimental Examples, when the waterproofing amount ratio was 3 or more, i.e., when the waterproofing amount was at least three times the waterproofing amount in Experimental Example 6, the waterproofing amount was rated "A (excellent)." When the waterproofing amount ratio was 1.5 or more and less than 3, the waterproofing amount was rated "B (good)." When the waterproofing amount ratio was less than 1.5, the waterproofing amount was rated "F (fail)."

Figure 8:
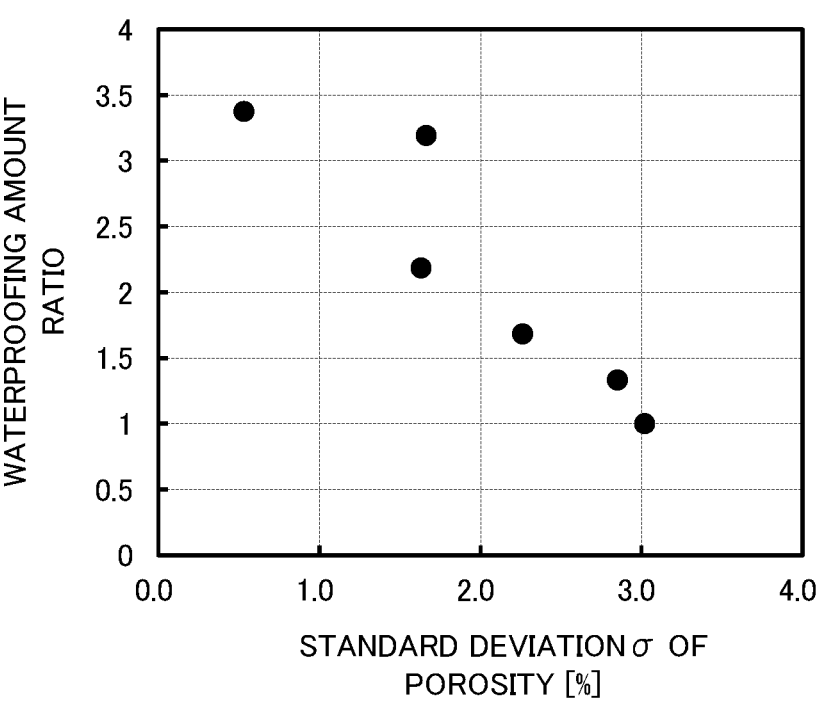
FIG. 8 is a graph showing the relation between the standard deviation σ of porosity and the ratio between waterproofing amounts.

The standard deviation σ in the inner protective layer 92, the waterproofing amount ratio, and the judgement result in each of Experimental Examples 1 to 6 are summarized in Table 1. FIG. 8 is a graph of the waterproofing amount ratio plotted against the standard deviation σ of the porosity in each of Experimental Examples 1 to 6.

TABLE 1

| | Standard deviation σ of prosity [%] | Waterproofing amount ratio | Judgement |
|---|---|---|---|
| Experimental Example 1 | 0.5 | 3.4 | A |
| Experimental Example 2 | 1.6 | 2.2 | B |

TABLE 1-continued

| | Standard deviation σ of prosity [%] | Waterproofing amount ratio | Judgement |
|---|---|---|---|
| Experimental Example 3 | 1.7 | 3.2 | A |
| Experimental Example 4 | 2.3 | 1.7 | B |
| Experimental Example 5 | 2.9 | 1.3 | F |
| Experimental Example 6 | 3.0 | 1.0 | F |

As can be seen from Table 1 and FIG. 8, in Experimental Examples 1 to 4 in which the standard deviation σ was 2.3% or less, the waterproofing amount was larger than that in Experimental Examples 5 to 6 in which the standard deviation σ was larger than 2.3%, and the waterproofing performance of the sensor element 101 was found to be improved. Specifically, in each of Experimental Examples 1 to 4, the waterproofing amount ratio was 1.5 or more, and the judgement result was A or B. However, in each of Experimental Examples 5 and 6, the judgement result was F. As can be seen from the results in Experimental Examples 1 to 6, the smaller the standard deviation G, the further the waterproofing performance tends to improve. As can be seen from the results in Experimental Examples 1 to 4, the waterproofing amount tends to change steeply at a point where the standard deviation σ is about 1.7%. The above results show that, when the standard deviation σ is 1.5% or less, the waterproofing performance of the sensor element 101 may be further improved.

The present application claims priority from Japanese Patent Application No. 2021-042258, filed Mar. 16, 2021, the entire contents of which are incorporated herein by reference. International Application No. PCT/JP2022/006368, filed on Feb. 17, 2022, is incorporated herein by reference in its entirety.

What is claimed is:

1. A gas sensor element comprising:

an element body including an oxygen-ion-conductive solid electrolyte layer; and a protective layer that covers at least part of the element body and is a porous body having a plurality of pores therein, wherein the standard deviation of the porosity of the protective layer is 2.3% or less, wherein the protective layer includes a porous inner protective layer and a porous outer protective layer that is located outward of the inner protective layer and has a smaller porosity than the inner protective layer, wherein the element body has an elongate rectangular parallelepiped shape and includes a measurement-object gas flow portion that is formed inside the element body and through which a measurement-object gas introduced thereinto flows, wherein the inner protective layer covers a closest surface of the element body that is one of four surfaces thereof extending in a longitudinal direction of the element body and that is closest to the measurement-object gas flow portion, and wherein, in the inner protective layer, the standard deviation of the porosity in a portion that covers a region of the closest surface onto which the measurement-object gas flow portion is projected is 2.3% or less.

2. The gas sensor element according to claim 1, wherein the porosity of the protective layer is from 10% to 40% inclusive.

3. The gas sensor element according to claim 2, wherein the standard deviation of the porosity of the protective layer is 1.5% or less.

4. The gas sensor element according to claim 1, wherein the standard deviation of the porosity of the protective layer is 1.5% or less.

5. A gas sensor comprising the gas sensor element according to claim 1.

6. A gas sensor element comprising:

an element body including an oxygen-ion-conductive solid electrolyte layer; and a protective layer that covers at least part of the element body and is a porous body having a plurality of pores therein, wherein the standard deviation of the porosity of the protective layer is 2.3% or less, wherein the protective layer includes a porous inner protective layer and a porous outer protective layer that is located outward of the inner protective layer and has a smaller porosity than the inner protective layer, wherein the element body has an elongate rectangular parallelepiped shape and includes a measurement-object gas flow portion that is formed inside the element body and through which a measurement-object gas introduced thereinto flows, wherein a gas inlet that is an inlet of the measurement-object gas flow portion has an opening on a longitudinal end surface of the element body, wherein the inner protective layer covers the end surface of the element body, and wherein, in the inner protective layer, the standard deviation of the porosity in a portion that covers the end surface is 2.3% or less.

7. The gas sensor element according to claim 6, wherein the standard deviation of the porosity of the protective layer is 1.5% or less.

8. A gas sensor element comprising:

an element body including an oxygen-ion-conductive solid electrolyte layer; and a protective layer that covers at least part of the element body and is a porous body having a plurality of pores therein, wherein the standard deviation of the porosity of the protective layer is 2.3% or less, wherein the protective layer includes a porous inner protective layer and a porous outer protective layer that is located outward of the inner protective layer and has a smaller porosity than the inner protective layer, wherein the standard deviation of the porosity in the inner protective layer is 2.3% or less, wherein the element body has an elongate rectangular parallelepiped shape and includes a measurement-object gas flow portion that is formed inside the element body and through which a measurement-object gas introduced thereinto flows, wherein the inner protective layer covers a closest surface of the element body that is one of four surfaces thereof extending in a longitudinal direction of the element body and that is closest to the measurement-object gas flow portion, and wherein, in the inner protective layer, the standard deviation of the porosity in a portion that covers a region of the closest surface onto which the measurement object gas flow portion is projected is 2.3% or less.

9. The gas sensor element according to claim 8, wherein the porosity of the inner protective layer is from 40% to 70% inclusive.

10. The gas sensor element according to claim 8, wherein the standard deviation of the porosity of the inner protective layer is 1.5% or less.

11. A gas sensor element comprising:

an element body including an oxygen-ion-conductive solid electrolyte layer; and a protective layer that covers at least part of the element body and is a porous body having a plurality of pores therein, wherein the standard deviation of the porosity of the protective layer is 2.3% or less, wherein the protective layer includes a porous inner protective layer and a porous outer protective layer that is located outward of the inner protective layer and has a smaller porosity than the inner protective layer, wherein the standard deviation of the porosity in the inner protective layer is 2.3% or less, wherein the element body has an elongate rectangular parallelepiped shape and includes a measurement-object gas flow portion that is formed inside the element body and through which a measurement-object gas introduced thereinto flows, wherein a gas inlet that is an inlet of the measurement-object gas flow portion has an opening on a longitudinal end surface of the element body, wherein the inner protective layer covers the end surface of the element body, and wherein, in the inner protective layer, the standard deviation of the porosity in a portion that covers the end surface is 2.3% or less.

12. The gas sensor element according to claim 11, wherein the standard deviation of the porosity of the inner protective layer is 1.5% or less.

\* \* \* \* \*